US00PP24880P3

(12) United States Plant Patent
Aiello et al.

(10) Patent No.: US PP24,880 P3
(45) Date of Patent: Sep. 16, 2014

(54) ***PRUNUS* PLANT NAMED 'CHESTNUT HILL'**

(50) Latin Name: *Prunus laurocerasus*
Varietal Denomination: Chestnut Hill

(75) Inventors: Anthony S. Aiello, Philadelphia, PA (US); Rochelle J. Dillard, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 142 days.

(21) Appl. No.: 13/507,182

(22) Filed: Jun. 12, 2012

(65) Prior Publication Data

US 2013/0333080 P1 Dec. 12, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Buchanan, Ingersoll & Rooney, PC

(57) ABSTRACT

A new and distinct *Prunus laurocerasus* plant of unknown parentage is provided. The new plant can be readily distinguished from other plants of the species including the 'Otto Luyken' cultivar (non-patented in the United States). A slow to moderate growth habit is displayed to form a compact generally rounded plant with dense foliage. The foliage is dark green in coloration and displays more glossiness on the upper surface than commonly observed for the 'Otto Luyken' cultivar. Superior resistance to Coryneum blight has been observed. The new plant is well suited for providing attractive ornamentation in a hedge, foundation planting, or when grown en masse.

1 Drawing Sheet

Botanical/commercial classification: *Prunus laurocerasus*/Cherry Laurel Plant.

Varietal denomination: cv. Chestnut Hill.

SUMMARY OF THE INVENTION

The new cultivar originated by selection from among a population of *Prunus laurocerasus* plants undergoing evaluation in a controlled planting area at Philadelphia, Pa., U.S.A. The parentage of the new cultivar is unknown. The seeds used for the planting had been collected from *Prunus laurocerasus* plants growing at Thessaly, Greece, during September 1991. A single plant of the new cultivar was selected in view of its unique combination of characteristics. Such new plant was assigned Accession No. 91-105*C and was carefully preserved and further evaluated. Had this new plant not been selected and preserved it would have been lost to mankind.

The new cultivar can be readily distinguished from common *Prunus laurocerasus* plants, including the widely grown 'Otto Luyken' cultivar (non-patented in the United States), in view of its unique combination of characteristics.

It was found that the new *Prunus laurocerasus* plant of the present invention displays the following combination of characteristics:

(a) displays an attractive more compact growth habit than the 'Otto Luyken' cultivar,
(b) displays a slow to moderate growth rate,
(c) displays attractive dense dark green foliage having more glossiness on the upper surface than commonly observed for the 'Otto Luyken' cultivar,
(d) is more resistant to Coryneum blight than the 'Otto Luyken' cultivar, and
(e) is well suited for providing attractive ornamentation.

It has been confirmed that the combination of characteristics of the new plant is reliably expressed.

The new cultivar can be grown to advantage as a hedge, foundation planting or mass planting. The attractive dark green foliage coloration commonly is maintained even during the winter months.

Superior resistance to bacterial and fungal pathogens in general has been observed during observations to date when compared to the 'Otto Luyken' cultivar.

The new cultivar also can be readily distinguished from the 'Gajo' cultivar (U.S. Plant Pat. No. 19,334) and the 'Greentorch' cultivar (U.S. Plant Pat. No. 22,327). More specifically, the growth habit of the 'Gajo' cultivar is more upright and the growth habit of the 'Greentorch' cultivar is more erect and columnar.

The new cultivar, unlike the species, commonly has been found to take pruning well, and is even capable of undergoing severe pruning to maintain a desired plant size while maintaining attractiveness. The slow to moderate growth rate also contributes to the maintenance of plant size. The new plant also has been found to tolerate salt spray during observations to date.

The new plant can be grown in full sun to shade. During observations to date, the plant has been found to grow best in part shade in well-drained soil that is amended with organic matter. It is preferred that the plant not be grown at a location where water commonly accumulates.

Asexual reproduction of the new cultivar has been repeatedly carried out at Philadelphia, Pa., U.S.A., and at West Grove, Pa., U.S.A., through the use of softwood cuttings. It has been demonstrated by such asexual reproduction that the new plant's characteristics are reliably transmitted from one generation to another in a true-to-type manner.

The new cultivar has been named 'Chestnut Hill'.

BRIEF DESCRIPTION OF THE PHOTOGRAPH

The accompanying photograph shows as nearly true as it is reasonably possible to make the same in a color illustration of this character, a typical specimen of the new cultivar. A plant at an age of approximately five years is shown while growing in the ground outdoors at West Grove, Pa., U.S.A. The plant had been asexually reproduced through the use of softwood cuttings and was grown in full sun. The photograph was obtained during August.

DETAILED BOTANICAL DESCRIPTION

The following is a detailed description of the new plant of the present invention which primarily was prepared during August while observing three-year-old plants growing in the ground at West Grove, Pa., U.S.A. The color terminology is in accordance with The R.H.S. Colour Chart (1995 or equivalent) of The Royal Horticultural Society, London, England, except when general color terms are used which are to be accorded their customary dictionary significance. The flower description was prepared while observing the originally selected plant of the new cultivar during the first week of May while growing at Philadelphia, Pa., U.S.A.

Botanical classification: *Prunus laurocerasus*.

Type: Hardy evergreen shrub for garden decoration and general landscape usage.

Plant:

- *Growth habit*.—Slow to moderate, compact, dense, generally rounded, and bushy.
- *Height*.—Approximately 60 cm at five years of age, and estimated to be approximately 120 cm meters at full maturity.
- *Width*.—Approximately 75 cm at five years of age, and estimated to be approximately 120 cm at full maturity.

Branches:

- *Length*.—Commonly approximately 20 to 25 cm on average.
- *Diameter*.—Commonly approximately 5 mm on average.
- *Internode length*.—Commonly approximately 1.5 to 2 cm on average.
- *Relative strength*.—Strong.
- *Texture*.—When young relatively smooth and glabrous, and when mature woody and rough.
- *Color*.—When developing near Yellow-Green Group 145A, and when mature Grey-Brown Group 199B.

Foliage:

- *Arrangement*.—Alternate, simple.
- *Length*.—Approximately 7.5 cm on average.
- *Width*.—Approximately 3 cm on average.
- *Shape*.—Narrowly elliptic.
- *Apex*.—Acute.
- *Base*.—Attenuate.
- *Margin*.—Entire, revolute, slightly undulate.
- *Texture*.—Smooth and glabrous on both surfaces.
- *Finish*.—Highly glossy on the upper surface.
- *Glands*.—Circular, approximately 1 mm in diameter, near Brown Group 200A in coloration, at a frequency of approximately 2 to 4 per leaf on the lower leaf surface near the base.
- *Venation*.—Pinnate.
- *Color*.—Yellow-Green Group 147A on the upper surface, and Yellow-Green Group 147B on the under surface.
- *Petiole*.—Length: approximately 1 cm on average. Diameter: approximately 2 mm on average. Texture: generally smooth and glabrous on upper and lower surfaces. Color: near Yellow-Green Group 144A on both surfaces.

Inflorescence:

- *Flowering*.—During observations to date, flowers are believed to have formed exclusively on the mother plant. Accordingly, the information that follows was obtained through the observation of the original plant while growing at Philadelphia, Pa., U.S.A.
- *Time*.—April to early May.
- *Frequency*.—Have not readily been observed other than on the originally selected plant of the new cultivar.
- *Type*.—Single rotate flowers on terminal and axillary racemes.
- *Size*.—Small.
- *Height*.—Approximately 5 mm on average.
- *Raceme length*.—Commonly approximately 2.5 to 4 cm on average.
- *Raceme width*.—Commonly approximately 13 mm on average.
- *Diameter*.—Approximately 10 mm on average.
- *Petal number*.—Five.
- *Petal size*.—Small and approximately 4 to 5 mm in length on average, and approximately 3 mm in width on average.
- *Petal form*.—Orbicular.
- *Petal apex*.—Rounded.
- *Petal margin*.—Sinuate.
- *Petal color*.—Near White Group 155A on both surfaces.
- *Number*.—When observed, approximately 20 to 25 flowers on average per raceme.
- *Length*.—Approximately 5 cm per raceme on average from the tip of the highest pedicellate flower to the tip of the lowest pedicellate flower during the 2012 growing season.
- *Stamen*.—Number: commonly approximately 15 per flower on average. Filament length: approximately 4 to 5 mm on average. Filament color: near White Group 155B. Anther color: commonly between White Group 155A and White Group 155B.
- *Pistil*.—Number: commonly one per flower. Length: approximately 5 mm on average. Texture: relatively smooth. Height: approximately the same as that of the anthers. Color: commonly between Green Group 143B and Green Group 143C.
- *Fragrance*.—Slight sweet aroma.
- *Lastingness*.—Commonly approximately 7 to 10 days on average depending on environmental conditions.
- *Sepals*.—Absent.
- *Pedicel*.—Length: approximately 4 mm on average. Width: approximately 1 mm on average. Color: commonly between Yellow-Green Group 144B and Yellow-Green Group 144C.
- *Peduncle*.—Length: approximately 5 mm on average. Diameter: approximately 2 mm on average. Texture: generally smooth. Color: near Green Group 141C.
- *Seeds/fruit*.—None encountered during observations to date.

Development:

*Tolerance to diseases*.—During observations to date has shown superior resistance to bacterial and fungal pathogens, particularly with respect to *Coryneum* blight (i.e., shot hole disease).

*Tolerance to rain, heat and wind*.—Good.

*Tolerance to cold*.—Proven winter hardy in U.S.D.A. Hardiness Zone No. 6b.

Plants of the new 'Chestnut Hill' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Prunus laurocerasus* plant having the following combination of characteristics:

(a) displays an attractive more compact growth habit than the 'Otto Luyken' cultivar, (b) displays a slow to moderate growth rate, (c) displays attractive dense dark green foliage having more glossiness on the upper surface than commonly observed for the 'Otto Luyken' cultivar, (d) is more resistant to *Coryneum* blight than the 'Otto Luyken' cultivar, and (e) is well suited for providing attractive ornamentation; substantially as illustrated and described.

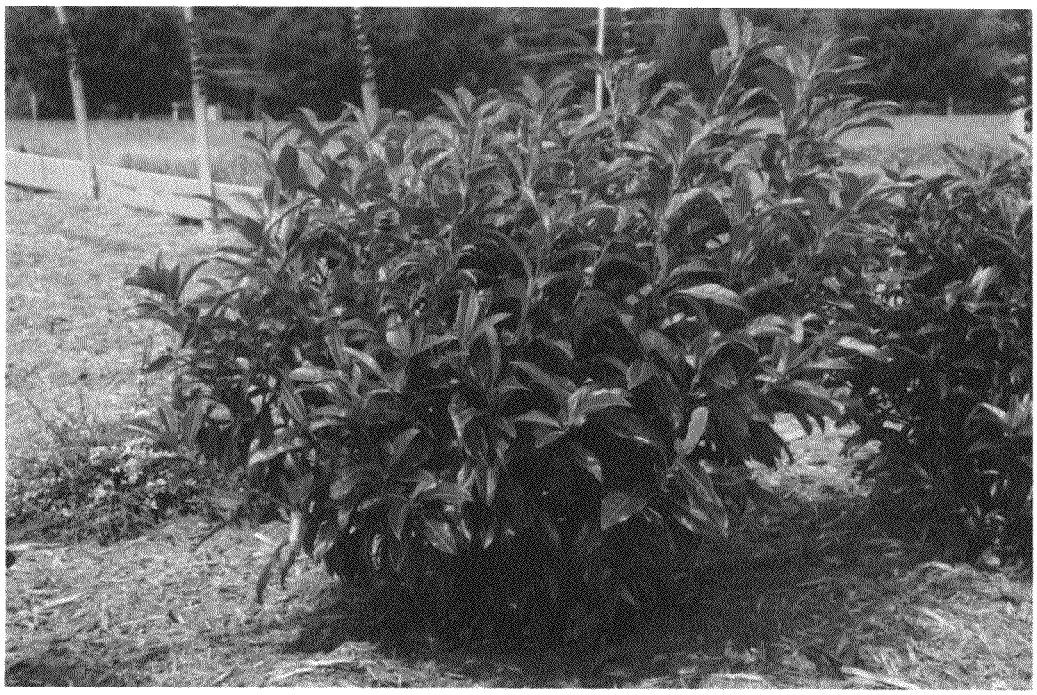

* * * * *